United States Patent [19]

Barud

[11] Patent Number: 5,410,767

[45] Date of Patent: May 2, 1995

[54] EXAMINATION TABLE CONNECTED TO A FLOOR STAND VIA AN ARTICULATED LEVER ARRANGEMENT

[75] Inventor: Sigvard Barud, Jaerfaella, Sweden

[73] Assignee: Siemens Elema AB, Solna, Sweden

[21] Appl. No.: 153,110

[22] Filed: Nov. 17, 1993

[30] Foreign Application Priority Data

Dec. 3, 1992 [SE] Sweden .................................. 9203643

[51] Int. Cl.6 ............................................... A61B 6/04
[52] U.S. Cl. .......................................... 5/601; 74/103;
74/490.04; 108/143; 108/20
[58] Field of Search .................... 5/600, 601; 378/209,
378/208; 74/479 BF, 479 BP, 103; 108/137,
143, 20, 103, 140, 22

[56] References Cited

U.S. PATENT DOCUMENTS

| | | | |
|---|---|---|---|
| 1,484,229 | 2/1924 | Miles | 108/140 |
| 2,680,314 | 6/1954 | Snyder | 108/140 |
| 3,627,250 | 12/1971 | Degrum | 378/209 |
| 3,843,112 | 10/1974 | McDonald . | |
| 4,687,167 | 8/1987 | Skalka | 108/103 |
| 4,706,515 | 11/1987 | Yosukawa | 74/479 BF |
| 4,838,181 | 6/1989 | Luyk | 108/143 |
| 4,885,988 | 12/1989 | Span | 378/209 |
| 5,013,018 | 5/1991 | Sicek et al. . | |
| 5,083,896 | 1/1992 | Uehara | 74/479 BF |

FOREIGN PATENT DOCUMENTS 0009463 9/1979 European Pat. Off. .
389332 9/1990 European Pat. Off. ............ 378/209

OTHER PUBLICATIONS

Siemens Brochure for "Koordinat Angio".

*Primary Examiner*—Flemming Saether
*Attorney, Agent, or Firm*—Hill, Steadman & Simpson

[57] ABSTRACT

An examination table has a patient support plate attached to a floor stand so as to be movable relative to the floor stand in the longitudinal direction of the support plate. The support plate is generally rectangular, and has one side which is longer than the other. The support plate is moved relative to the floor stand by a motorized articulated lever, having first and second arms. Respective ends of the two arms are joined so as to be rotatable around a second shaft, and an opposite end of the first arm is rotatable around a first shaft connected to the support plate, and an opposite end of the second arm is rotatable around a third shaft attached to the floor stand. All three shafts are oriented perpendicularly to a horizontal plane in which the support plate is disposed, so that the first and second arms always move in a plane parallel to this horizontal plane. The articulated lever is operated in a controlled manner so that the angle between the long side of the support plate and the first arm is always equal to the angle between the long side of the support plate and the second arm for all positions.

7 Claims, 5 Drawing Sheets

EXAMINATION TABLE CONNECTED TO A FLOOR STAND VIA AN ARTICULATED LEVER ARRANGEMENT

BACKGROUND OF THE INVENTION

1. Field of the Invention

The present invention is directed to an examination table, suitable for supporting a patient during a medical examination, such as an x-ray examination, of the type having a patient support plate and a support stand, with means for displacing the support plate relative to the floor stand along the longitudinal direction of the support plate.

2. Description of the Prior Art

It is important for conducting x-ray examinations, for example, in combination with catheterizations, that the x-ray tube and the x-ray tube and the image carrier, which are mounted in common on an x-ray examination stand, have good access to the patient. In such examinations, the examination table and the x-ray examination stand are usually displaceable parallel to each other, so that, for example, the x-ray tube and the image carrier can be displaced from the head end to the foot end of the examination table as needed. This means that space must be present beneath the entire length of the support plate so that the image carrier can be moved along the longitudinal direction of the support plate beneath the support plate.

An examination table of this type which is suitable for conducting such examinations is described in the Siemens Brochure for the "KOORDINAT ANGLO" table. The support plate in this table rests on a fixed floor stand, and can be displaced with a telescoping rail system secured to the floor stand, so that the entire length of the support plate can be made to project from the floor stand. The floor stand is provided for the purpose of partially accepting a film changer, and partially accepting mechanisms for tilting the support plate. As a consequence, the floor stand is relatively large, has a complicated structure, and is thus expensive to manufacture.

Another examination table is disclosed in U.S. Pat. No. 5,013,018 which offers free space for the x-ray examination stand. The support plate in this table has a long side which is rigidly connected to a column-like floor stand. Displacement of the support plate in the longitudinal direction thereof ensues by means of floor rails. Floor rails are always considered to be an impediment in an examination room, and moreover, it is difficult to maintain such floor rails clean in the manner required in a clinical environment.

SUMMARY OF THE INVENTION

It is an object of the present invention to provide an examination table of the type having a floor stand and a support plate which is longitudinally displaceable thereon which is comparatively simple in structure and which provides good access for an x-ray examination stand.

The above object is achieved in accordance with the principles of the present invention in an examination table having a support plate which is longitudinally displaceable relative to a floor stand by means of an articulated lever system connecting the support plate to the floor stand, the articulated lever system having at least two arms which are rotatably connected to each other around a first shaft. A free end of the first arm is rotatably connected to the support plate around a second shaft, and a free end of the second arm is rotatably connected to the floor stand around a third shaft. The first, second and third shafts are all vertically disposed relative to the horizontal plane of the support plate, so that the first and second arms always move parallel to this plane. The articulated lever system is controllable so that the angle between the long side of the support plate and the first arm is equal to the angle between the long side of the support plate and the second arm for all positions. The support plate does not rest directly on the floor stand, and therefore the floor stand can be maintained relatively small in size. Moreover, the support plate can execute extremely long translational movements as a result of the articulated lever in comparison to conventional examination tables.

In one embodiment of the invention, the arms of the articulated lever are disposed in different parallel planes. In this manner, the articulated lever, proceeding from the point at which it is fastened to the floor stand, can be extended to the same extent in all directions.

In a further embodiment of the invention the free end of the first arm is connected at one end of the support plate, preferably the foot end thereof. This results in no parts being present beneath the support plate which would constitute an impediment for conducting an x-ray examination, and further permits the support plate to be projected to maximal extent from the floor stand.

In another embodiment of the invention, the individual lengths of the respective arms do not exceed the largest width of the support plate. This ensures that the arms do not project beyond the long side of the support plate, as the support plate is displaced along its longitudinal axis.

In another embodiment of the invention, the articulated lever is controlled by means of three motors, a first motor rotating the second arm around the third shaft, a second motor rotating the first arm around the first shaft, and a third motor rotating the support plate around the second shaft. This results in the support plate being automatically displaceable to any desired position. The motors are preferably stepping motors which displace the support plate step-by-step in the longitudinal direction thereof. Such movements are advantageous in conducting x-ray examinations, particularly in combination with a leg catheterization.

In another embodiment of the invention the articulated lever system includes a first gear wheel which is firmly attached to the floor stand around the third shaft, and is disposed within the free end of the second arm. A second gear is firmly fixed at the end of the first arm at the location of the first shaft, and is contained within the end of the second arm at that location. Transmission means are provided between the first and second gear wheels, and the first and second gear wheels are dimensioned so that a transmission ratio of 2:1 results. The articulated lever system further has a third gear wheel arranged around the first shaft and contained within first arm and rigidly connected to the second arm. A fourth gear wheel is contained within the first arm and is rotatable around the second shaft and is rigidly connected the support plate. Transmission means are provided between the third and fourth gear wheels and the third and fourth gear wheels are dimensioned so that a transmission ratio of 1:2 results. As a consequence of this structure of the articulated lever system, the support plate, when displaced, is forced to execute a translational motion in its longitudinal direction. Such a displacement of the support plate is preferably capable of being manually implemented. The second arm, however, can also be rotated by means of a motor, for example a stepping motor, so that an automatic displacement of the support plate is also possible given this embodiment of the articulated lever system.

DESCRIPTION OF THE PREFERRED EMBODIMENTS

Figure 1:
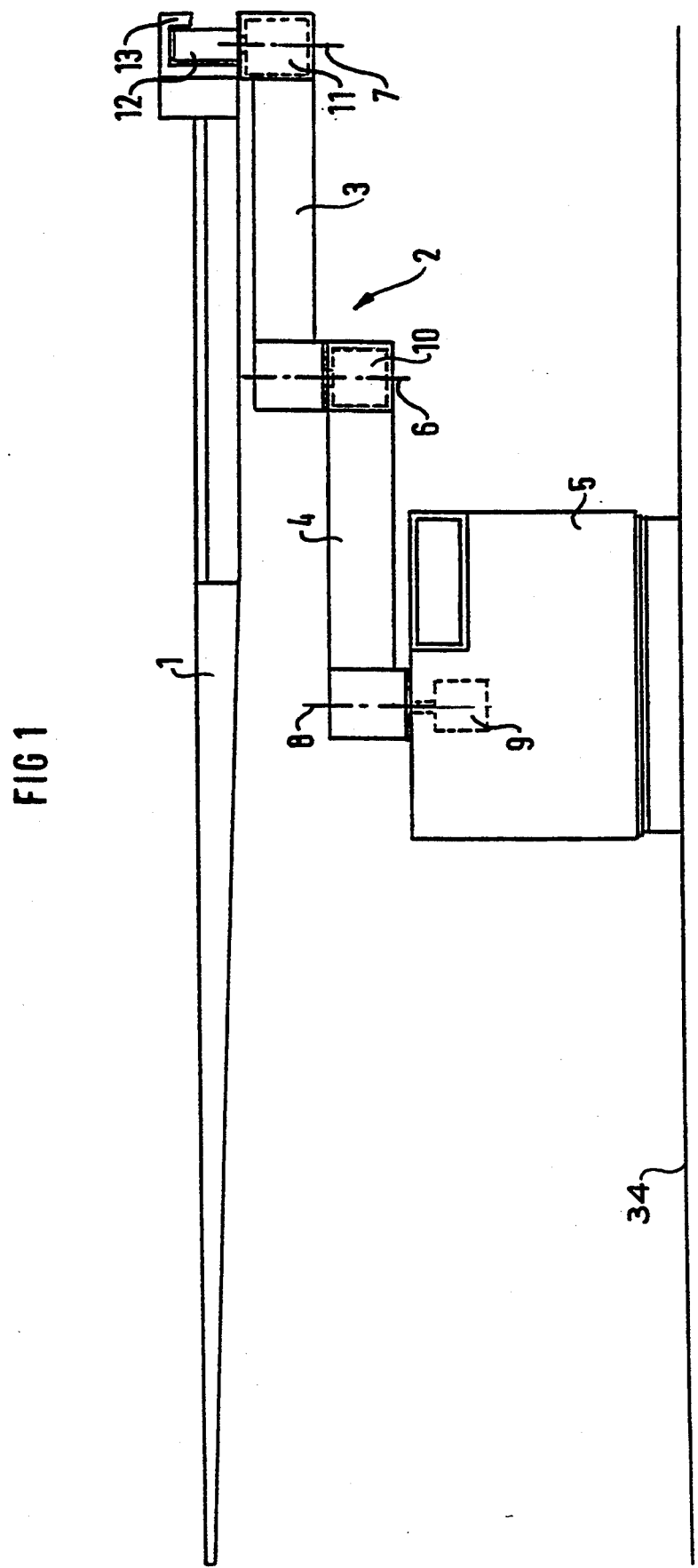
FIG. 1 is a side view of an examination table constructed in accordance with the principles of the present invention.

FIG. 1 shows an examination table having a support plate 1 connected to a height-adjustable floor stand 5 by means of an articulated lever system 2. The floor stand 5 is disposed on the floor 34 of an examination room. The articulated lever system 2 includes a first arm 3 and a second arm 4. One end of the first arm 3 is joined to one end of the second arm 4 in a rotatable manner around a first shaft 6. The other end of the first arm 3 is rotatably connected to the foot end of the support plate 1 at a second shaft 7. The other end of the second arm 4 is rotatably connected to the floor stand 5 around a third shaft 8. The end of the first arm 3 at the second shaft 7 is provided with an upwardly projecting bearing 12, which is connected to a rail 13 which is firmly attached to the foot end of the support plate 1. The rail 13 is displaceable on the bearing 12. The shafts 6, 7 and 8 are vertically disposed relative to the horizontal plane of the support plate 1, so that the first and second arms 3 and 4 always move parallel to this horizontal plane.

Figure 2:
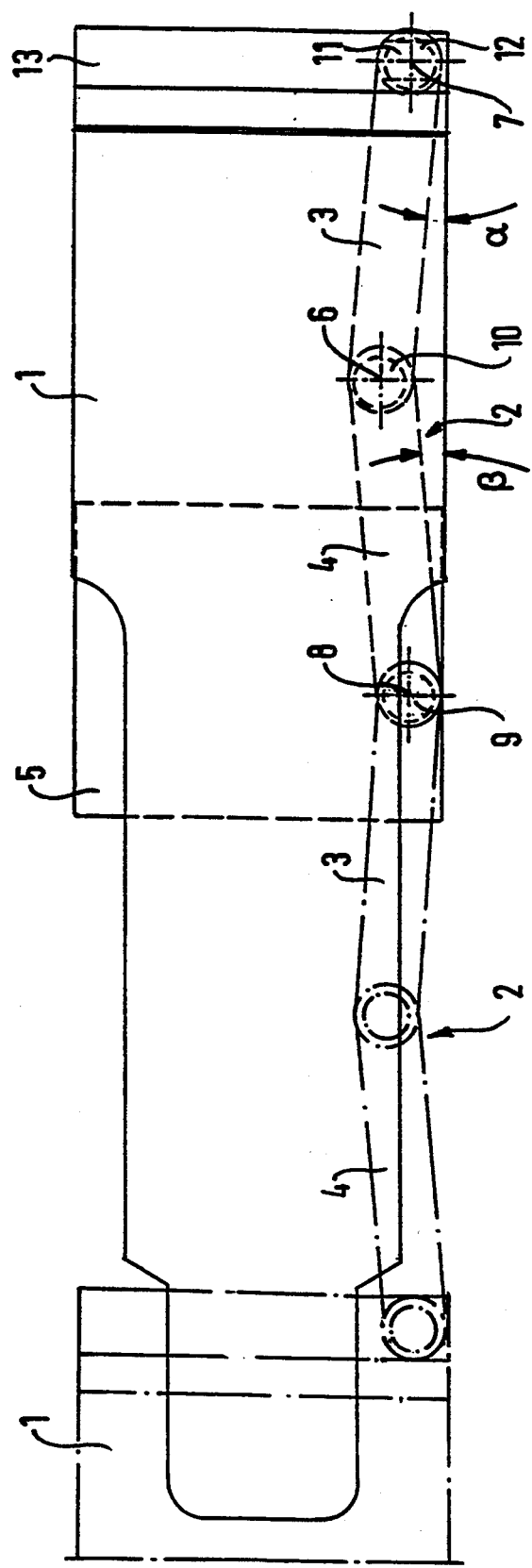
FIGS. 2 and 3 are plan views of the examination table of FIG. 1 respectively showing different stages in the longitudinal displacement thereof.

The control of the articulated lever system 2, and thus the control of the support plate 1, in this exemplary embodiment ensues by means of three motors 9, 10 and 11. The first motor 9, which is mounted in the floor stand 5, rotates the second arm 4 around the third shaft 8. The second motor 10 is disposed in the second arm 4 and rotates the first arm 3 around the first shaft 6. The third motor 11 is disposed in the first arm 3 and rotates the support plate 1 around the second shaft 7. The motors 9, 10 and 11 thus control the articulated lever system 2 so that an angle $\alpha$, as shown in FIG. 2, between the long side of the support plate 1 and the first arm 3 is equal to an angle $\beta$ between the long side of the support plate 1 and the second arm 4 in all positions. It is thus assured that the support plate is shifted along its longitudinal direction when the motor 9 rotates the second arm 4 around the third shaft 8. Means for controlling motors set forth in this exemplary embodiment are known from robotics technology, and are therefore not specified in greater detail. The position of the articulated lever system 2 and the support plate 1 shown with dot-dash lines in FIG. 2 illustrates an extreme position to which the support plate 1 can be shifted. It is also shown in FIG. 2 that the rail 13 extends along the entire narrow side of the support plate 1. In this manner, the support plate I can be shifted on the bearing 12 in a direction perpendicular to the longitudinal direction of the support plate 1. The support plate 1 can be shifted in this direction by an amount roughly corresponding to the width of the support plate 1. Such a displacement can be manually undertaken, so that the support plate 1 can be locked in a desired lateral position by means of a known locking mechanism, which is not separately shown.

Figure 3:
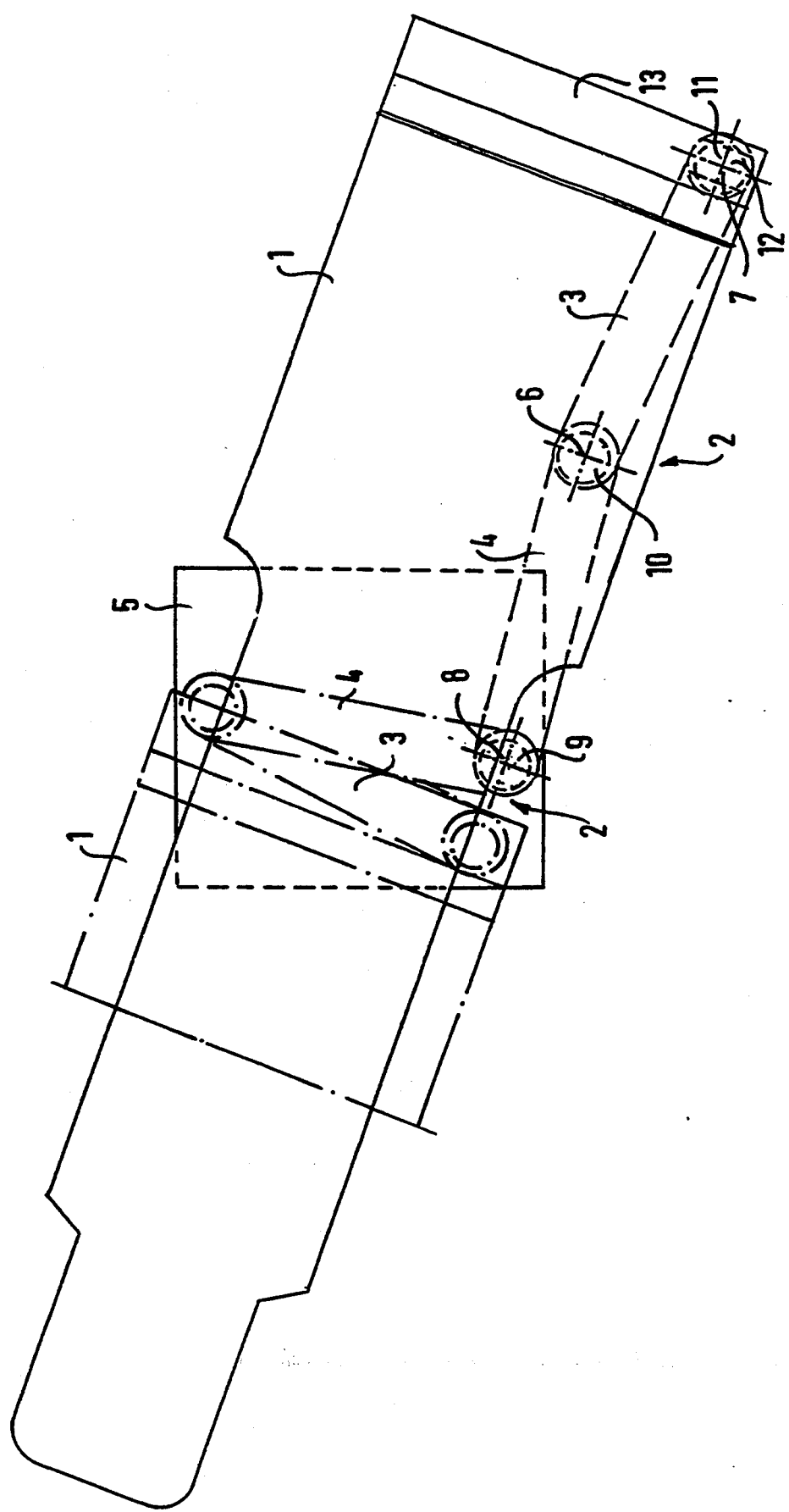

As shown in FIG. 3, the support plate I can be rotated around the third shaft 8 to a desired position relative to the floor stand 5. The support plate 1 can then be displaced in the longitudinal direction in the manner described above proceeding from any such rotated position. Because the length of the arms 3 and 4 does not exceed the largest width of the support plate 1, the arms 3 and 4 will not project beyond the sides of the support plate 1, even when they assume a position that is perpendicular to the long side of the support plate 1. The dot-dash position of the articulated lever system 2 and of the support plate 1 in FIG. 3 shows that the support plate 1 is shifted to a position wherein the arms 3 and 4 have assumed a position which is substantially perpendicular relative to the long side of the support plate 1.

Figure 4:
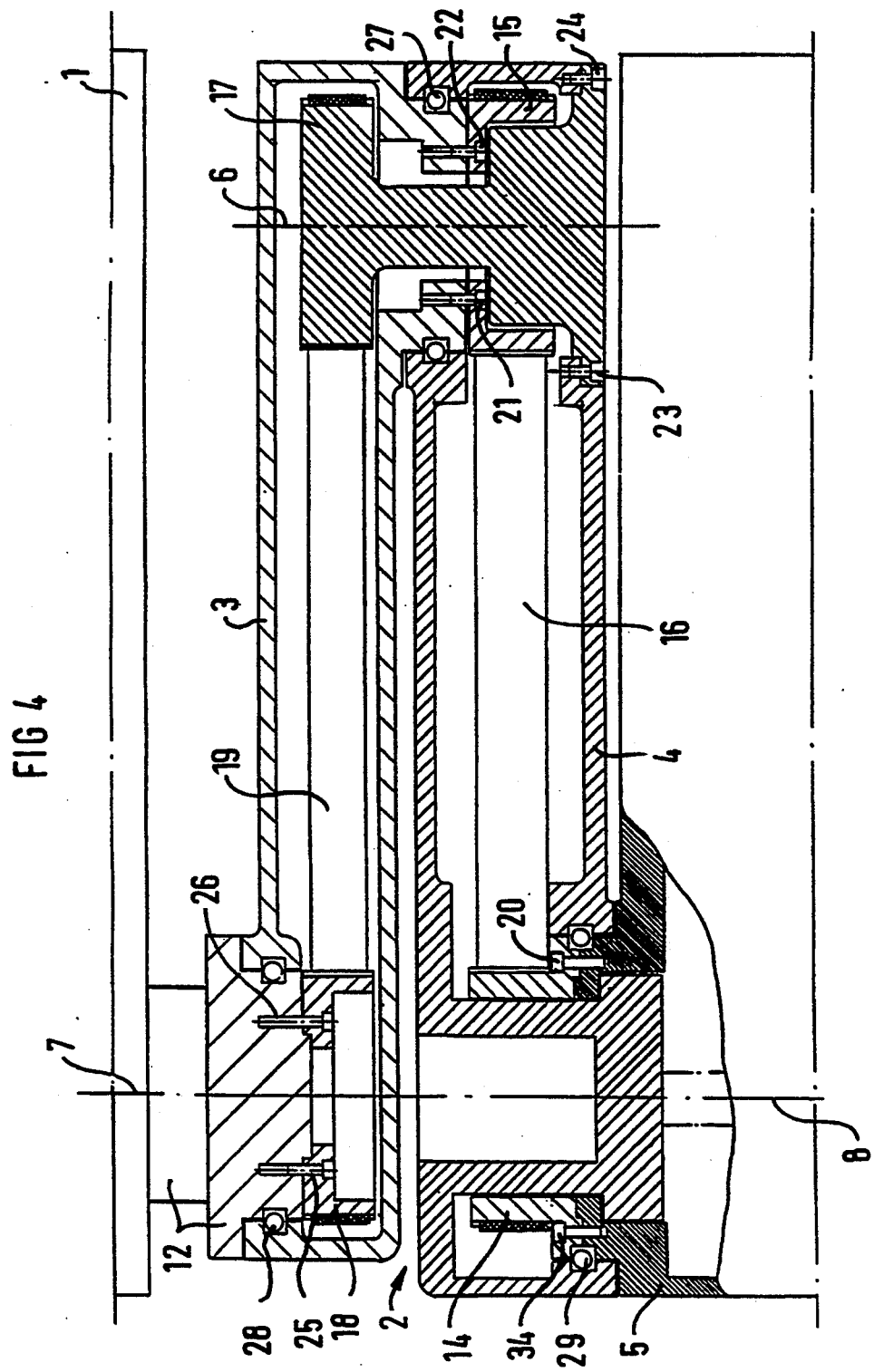
FIG. 4 is a side view showing details of an articulated lever system used in the examination table of the invention, the lever system being shown in section.

In the exemplary embodiment shown in FIG. 4, the articulated lever system 2 is controlled by a belt or chain transmission means, instead of the motors 9, 10 and 11. In this embodiment, the articulated lever system 2 includes a gear wheel 14 which is rigidly attached to the floor stand 5. The gear wheel 14 is arranged around the third shaft 8, is contained within the second arm 4. A second gear wheel 15 is rotatable around the first shaft 6, and is rigidly connected to the first arm 3 and contained within the second arm 4. A belt or chain 16 is arranged around the gear wheels 14 and 15. The articulated lever system 2 also includes a third gear wheel 17 contained within the first arm 3, and arranged around the third shaft 8 and rigidly connected to the second arm 4. A fourth gear wheel 18 is contained within the first arm 3. The first arm 3 is rotatable around the second shaft 7, and is rigidly attached to the support plate 1 via the bearing 12. A belt or chain 19 is arranged around the gear wheels 17 and 18.

The attachment of the gear wheels 14, 15, 17 and 18 to the respective, aforementioned elements is indicated in FIG. 4 with two screws. Accordingly, the gear wheel 14 is rigidly attached to the floor stand 5 by means of screws 20 and 34. The gear wheel 15 is secured to the first arm 3 by the screws 21 and 22. The gear wheel 17 is attached to the second arm 4 by screws 23 and 24. The gear wheel 18 is secured to the bearing 12, and thus to the support plate 1, by screws 25 and 26. The first and second arms 3 and 4 are rotatably connected to each other around the shaft 6 by means of a ball bearing 27. The other end of the first arm 3 is attached around the second shaft 7 to the bearing 12 by means of a ball bearing 28. The other end of the second arm 4 is rotatably connected to the floor stand 5 around the third shaft 8 by a ball bearing 29.

Figure 5:
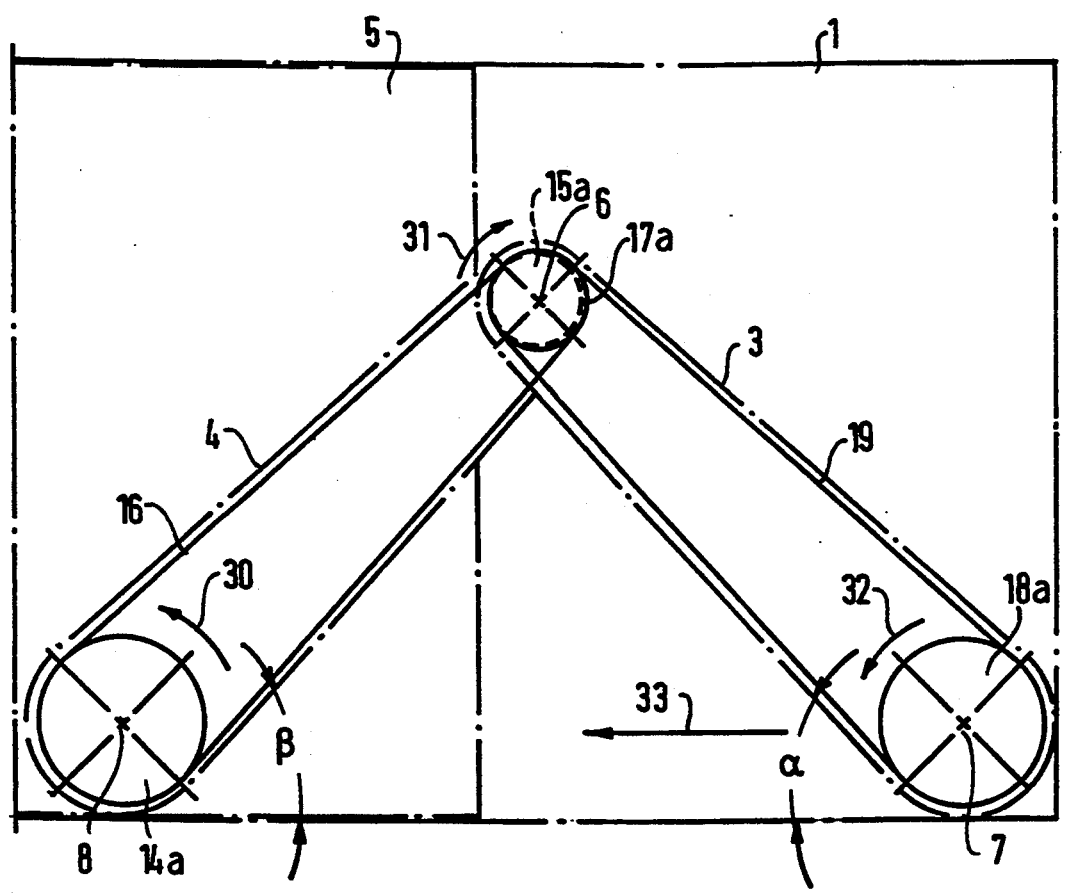
FIG. 5 is a schematic illustration of the articulated lever system of FIG. 4 in a plan view.

The control of the articulated lever system 2, and thus of the support plate 1, is described in greater detail with reference to FIG. 5, which shows a schematically illustrated articulated lever system 2, having the structure shown in more detail in FIG. 4, with gear wheels 14a, 15a, 17a and 18a corresponding in position to gear wheels 14, 15, 17 and 18. When the second arm 4 is rotated around the third shaft 8 in the direction of the arrow 30, the gear wheel 15a (because the gear wheel 14a is rigidly attached to the floor stand 5) is caused to forced to rotate by means of the teeth or openings of the belt or chain 16, so that the gear wheel 15a is rotated in the direction of the arrow 31. Due to a 2:1 transmission ratio between the gear wheels 14a and 15a, the first arm 3 is pivoted twice as much as the second arm 4, but in the opposite direction, due to its rigid connection to the gear wheel 15a. The gear wheel 17a in the first arm 3, which is rigidly attached to the second arm 4 and therefore follows the movements of the second arm 4, now forces the gear wheel 18a (which has a 2:1 transmission ratio relative to the gear wheel 17a) to move within the belt or chain 19, so that the gear wheel 18a is rotated in the direction of the arrow 32. Due to the successive rotation of the gear wheel 18a in relationship to the motion of the first arm 3, the support plate 1 is aligned in each position, so that the support plate 1 describes a translational motion in the direction of the arrow 33. The angle between the long side of the support plate 1 and the second arm 4 is always equal to the angle between the long side of the support plate 1 and the first arm 3.

The movements of the belt or chain driven articulated lever system 2, of course, can alternatively be controlled by a motor which drives the arm 4 around the third 8. The support plate 1 should also be capable of being manually displaced, so that a user can push the support plate 1 into a desired position. The support plate 1 can then be locked in any position with known locking means, which are not separately shown. The support plate 1 can also be freely mounted so that it is simultaneously movable both in the longitudinal and transverse directions.

Although modifications and changes may be suggested by those skilled in the art, it is the intention of the inventor to embody within the patent warranted hereon all changes and modifications as reasonably and properly come within the scope of his contribution to the art.

I claim as my invention:

1. An examination table comprising, for use in an examination room having a floor:
   a floor stand disposed on and extending above the floor;
   a support plate disposed in a horizontal plane on said floor stand, said support plate having a longitudinal axis and a long side substantially parallel to said longitudinal axis; and
   means for displacing said support plate along said longitudinal axis relative to said floor stand, said means for displacing including an articulated lever system comprising a first arm having first and second ends and a second arm having first and second ends, said second ends of said first and second arms being rotatably connected together around a first shaft, said first end of said first arm being rotatably connected to said support plate around a second shaft extending beneath said support plate, and said first end of said second arm being rotatably connected to said floor stand around a third shaft, said first, second and third shafts being vertically disposed relative to said horizontal plane, and said first, second and third shafts being operatively interconnected by a mechanical linkage means for causing said first and second arms always to move parallel to said horizontal plane, and for causing said first arm to make an angle between said first arm and said long side of said support plate which is equal to an angle between said long side of said support plate and said second arm for all positions of said support plate.

2. An examination table as claimed in claim 1 wherein said first and second arms are disposed in different, parallel planes.

3. An examination table as claimed in claim 1 wherein said support plate has a foot end, and wherein said first end of said first arm is connected to said support plate at said foot end.

4. An examination table as claimed in claim 1 wherein said first end of said first arm is connected at an end of said support plate, and further comprising means for mounting said support plate for permitting displacement of said support plate in a direction perpendicular to said longitudinal axis.

5. An examination table as claimed in claim 1 wherein said support plate has a largest width, and wherein said first and second arms each have a length which does not exceed said largest width.

6. An examination table as claimed in claim 1 wherein said third shaft is rotatably mounted relative to said floor stand for permitting rotation of said support plate around said third shaft relative to said floor stand.

7. An examination table as claimed in claim 1 wherein said mechanical linkage means includes:
   a first gear wheel rigidly attached to said floor stand and disposed around said third shaft and within said second arm;
   a second gear wheel rotatable around said first shaft and rigidly connected to said first arm and contained within said second arm;
   transmission means connected between said first and second gear wheels for causing relative rotation of said first and second gear wheels, said first and second gear wheels having dimensions for providing a transmission ratio of 2:1 therebetween;
   a third gear wheel disposed around said first shaft and rigidly connected to said second arm and contained within said first arm;
   a fourth gear wheel rigidly attached to said support plate and rotatably around said second shaft and contained within said first arm; and
   transmission means connected between said third and fourth gear wheels for causing relative rotation between said first and second gear wheels, said first and second gear wheels having dimensions for providing a transmission ratio of 1:2 therebetween.

* * * * *